(12) United States Patent
Nufer

(10) Patent No.: US 10,034,267 B2
(45) Date of Patent: Jul. 24, 2018

(54) METHOD AND APPARATUS FOR LOCALIZING COMPONENTS AND/OR PERSONS ASSIGNED TO AN IMAGE RECORDING SCANNER IN A SPATIAL ENVIRONMENT

(71) Applicant: Siemens Healthcare GmbH, Erlangen (DE)

(72) Inventor: Stephan Nufer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/404,373

(22) Filed: Jan. 12, 2017

(65) Prior Publication Data

US 2017/0201962 A1 Jul. 13, 2017

(30) Foreign Application Priority Data

Jan. 12, 2016 (DE) .......................... 10 2016 200 239

(51) Int. Cl.
*H04W 64/00* (2009.01)
*H04L 29/08* (2006.01)
*G16H 40/63* (2018.01)

(52) U.S. Cl.
CPC .......... *H04W 64/003* (2013.01); *G16H 40/63* (2018.01); *H04L 67/18* (2013.01); *H04L 67/12* (2013.01)

(58) Field of Classification Search
CPC .............................. H04W 64/003; H04L 67/18
USPC ........ 455/456.1; 340/524; 701/516; 709/205
See application file for complete search history.

(56) References Cited

U.S. PATENT DOCUMENTS

| | | | | |
|---|---|---|---|---|
| 2006/0187044 | A1* | 8/2006 | Fabian | A61B 5/06 340/572.1 |
| 2008/0030345 | A1* | 2/2008 | Austin | A61B 90/90 340/572.8 |
| 2009/0037244 | A1* | 2/2009 | Pemberton | G06Q 10/087 705/28 |
| 2012/0088523 | A1* | 4/2012 | Shirakawa | G06Q 10/10 455/456.3 |
| 2015/0168154 | A1* | 6/2015 | Boerger | G06Q 10/1095 701/410 |

(Continued)

FOREIGN PATENT DOCUMENTS

| | | |
|---|---|---|
| CA | 2 595 830 A1 | 2/2009 |
| WO | WO-94/22098 A1 | 9/1994 |

OTHER PUBLICATIONS

Wikipedia article for iBeacon, (2016).

*Primary Examiner* — Inder Mehra
(74) *Attorney, Agent, or Firm* — Schiff Hardin LLP

(57) ABSTRACT

In a method and system for localizing optional and/or exchangeable components of at least one image recording scanner and/or for localizing persons assigned to the image recording scanner in a spatial environment around the location of the image recording scanner, the components and/or persons are each provided with a wireless transmit device and the environment is provided with wireless receive devices. For each transmit device, using at least one localization signal received by at least one receive device in which the transmitting transmit device is identified, an item of position information of the transmit device, and thus of the component or person assigned to the transmit device, is determined and is provided in a computer for recall purposes.

16 Claims, 2 Drawing Sheets

(56) References Cited

U.S. PATENT DOCUMENTS

| | | |
|---|---|---|
| 2015/0213225 A1 | 7/2015 | Amarasingham et al. |
| 2015/0339450 A1 | 11/2015 | Allen-Raffl et al. |
| 2015/0369612 A1* | 12/2015 | Nishimura ........... G01C 21/206 |
| | | 701/537 |
| 2015/0379576 A1* | 12/2015 | Otis ................... G06Q 30/0261 |
| | | 705/14.53 |
| 2016/0116976 A1* | 4/2016 | Russell ................. G06Q 10/00 |
| | | 340/10.5 |
| 2016/0140828 A1* | 5/2016 | DeForest ............ G06F 19/3418 |
| | | 340/539.12 |

* cited by examiner

METHOD AND APPARATUS FOR LOCALIZING COMPONENTS AND/OR PERSONS ASSIGNED TO AN IMAGE RECORDING SCANNER IN A SPATIAL ENVIRONMENT

BACKGROUND OF THE INVENTION

Field of the Invention

The invention concerns a method and a system for localizing optional and/or exchangeable components of at least one image recording scanner and/or persons assigned at least temporarily to the image recording scanner in a spatial environment around the location of the image recording scanner.

Description of the Prior Art

Many image recording scanners have been designed to be modular so that certain components can be exchanged or can be added as an optional extension. Therefore for a magnetic resonance apparatus as an image recording scanner, various push-fit local coils and body coils, which are not permanently integrated as well as dockable, mobile patient couches exist, for instance. Similarly for x-ray devices as image recording scanners, various types of mobile detectors and/or patient couches which can be used are known.

The optional and/or exchangeable components are, in the case of magnetic resonance apparatuses, in most cases not mounted in the same room as the image recording scanner, but are, instead disposed in different rooms or corridors, particularly if larger radiology practices, radiology departments and/or hospitals are considered as the environments. One massive problem here is that the ability to locate such a component is dependent on the organization of the person last using and/or transporting the component. Therefore employees in radiology departments/practices as environments with, in most instances, a number of image recording scanners are consequently encouraged to be organized, since otherwise a complicated manual search is required.

Similar problems occur, especially in larger radiology departments as environments that often have a number of image recording scanners, with patients who are possibly not familiar with the large environments and who wait for their examination at the wrong place and/or fall asleep. A manual search and/or call for the respective patient is likewise required here. Moreover, some patients may be restricted in terms of mobility and may not respond correctly to the call process.

SUMMARY OF THE INVENTION

An object of the invention is to provide such an imaging scanner with the capability of locating components and/or persons, in particular patients, within a predetermined environment, in particular in radiology departments having a number of image recording scanners, in an improved manner.

This object is achieved in accordance with the invention by a method of the type cited above, wherein the components and/or persons are provided with a wireless transmit device and the environment is provided with wireless receive devices, wherein for each transmit device, via at least one localization signal received by at least one receive device and that identifies the transmitting transmit device, an item of position information of the transmit device and thus of the component or person (source) assigned to the transmit device, is determined, and this identification is provided in a computer for recall purposes.

The invention therefore solves the problem with small transmit devices, which each wirelessly emit a localization signal that identifies the transmit device and permits a localization, in other words a determination of the position information, when it is received by a (preferably) stationary receive device that is present in the environment. For identification purposes, a Universally Unique Identifier (UUID) can be respectively assigned to the individual transmit devices, for instance. Since the identification information, in particular the UUID, contained in the localization signal in the computer is assigned to the corresponding component or person, the corresponding component or person can thus be localized by the transmit device by an item of position information describing the position of the component or person being determined. Each of the components or each person, in particular each patient, can therefore be equipped with a transmit device of this type, which can emit a localization signal with a suitable item of identification information. The receive devices disposed in the environment, which is preferably a radiology department with a number of image recording scanners, can thus detect which components/persons are present and where they are located.

By combining transmit devices on components/persons and detecting localization signals of these transmit devices in the corresponding environment, sought components/persons can be more quickly and easily located with the use of suitable applications, which may also be web-based, for instance.

It should be noted that this method can naturally be extended to further additional objects to be localized, which can then likewise be provided with a transmit device and consequently be localized with the use of the receive devices.

As mentioned, it is preferable for stationary receive devices to be used, wherein the position information is determined by taking the fixed position of the receive device into account. For instance, it is in practice conceivable for the determination of the position information to be made on the basis of the reception strength of the localization signal in at least one receive device. Localization methods of this type are known in other fields, for instance within the scope of navigation in bearing housings (logistics) and such, as well as for navigation over a larger scale. If reception strengths of the localization signal can be determined in a number of receive devices, a triangulation for an improved and more accurate position determination is possible, wherein one development of the invention can also provide for a receive device to be assigned to each room in the environment, this is thus arranged in the room and the position information comprises an assignment to a room. In this case, a receive device can be installed in each room for instance, also including corridors, in the environment, in particular a radiology department, the receive device is thus able to detect which objects/persons are disposed in the room. To this end the reception strength can naturally be used in turn if receive devices in different rooms receive the localization signal. Nonetheless, it should be noted that in addition to the assignment, a triangulation in rooms is naturally also possible, for instance by a number of receive devices being arranged in rooms and corridors.

For wireless communication between the transmit devices and the receive devices, radio waves are preferably used, wherein the communication is carried out according to Bluetooth standard and/or the transmit device emits the localization signal cyclically as a broadcast. Appropriate for use within the scope of the inventive method is, for instance, the proprietary standard for navigation in closed rooms that was introduced by Apple Inc. under the brand name iBeacon. The transmit device (beacons) there emit localization signals at fixed time intervals. The Bluetooth Low Energy (BLE) technology also used in particular in iBeacon, which operates in an extremely power-saving manner and thus minimizes time-consuming battery replacement or charging processes, lends itself in particular to data transmission.

In an embodiment of the method, in order to provide persons with the transmit device, to attach an armband containing or carrying the transmit device to the person, particularly for patients as persons who are registering for an examination with the at least one image recording scanner. Within this embodiment, an interface is also provided, in order to register or deregister new components/persons equipped with transmit devices in the system realized by the inventive method. For instance, patients can be registered by a registration process at a reception are or the like by issuing an armband having the transmit device, or deregistered by handing back the armband. The latter can then take place when the armband is given back after the examination and/or treatment has been performed.

Independently of the application of the method to persons, in particular patients, it is advantageous to create a suitable sub-method for registration and deregistration, by a corresponding user interface being made available by the computer or a further computer, for instance a workplace computer, in which the corresponding assignment to the components/the person is created when a transmit device is used. If patients, as described, are the persons with transmit devices, it is expedient to realize the registration by using what is known as a DICOM Modality Worklist (DMWL) in order to link the worklist into the overall medical context. In this case the registration, similar to the deregistration, at least of patients, thus can be carried out by updating the DMWL.

At least one patient couch and/or at least one detector and/or at least one local coil with a transmit device can be provided as components. A number of other optional and/or exchangeable components of image recording scanners are also conceivable. As mentioned, the environment is preferably a radiology department, with radiology practices also being included in this term. A radiology department of this type then in most cases has a number of image recording scanners, for instance at least one magnetic resonance device and at least one x-ray device, which have different components that can be removed from the respective image recording scanner and that are preferably all provided with transmit devices.

In an embodiment of the present invention at least the components in the computer are registered and, when localization signals of a component are not received, at least one warning message indicating the inability to localize (find) the component is emitted. While reference has already been made to the registration/deregistration, the fact that components that should be present are known to the computer can be used to make the unauthorized removal of objects, in particular components, from the environment, noticeable. In this way an alarm can be emitted for instance, an item of position information for a component can no longer be determined because localization signals therefrom can no longer be detected. Theft/unauthorized removal can thus be noticed and ideally also avoided.

In an embodiment, sub-environments of the environment can also be defined and assigned to components, and if position information no longer can be determined and/or the position information indicates a position of the component outside of the sub-environment assigned thereto, at least one warning message indicating that the component is leaving the sub-environment is emitted. In this way the monitoring of correct transactions with respect to the components can thus be further improved.

It is particularly advantageous for an item of position information relating to at least one component and/or at least one object to be recalled by a mobile device and indicated thereupon. A mobile device of this type is preferably a tablet PC, which can be worn by persons working in the environment, for instance employees in the radiology department. Other similar mobile devices are also conceivable, for instance mobile phones. These mobile devices can if they are not already part of the computer itself, communicate with the computer, for instance via WLAN, in order to indicate position information that helps to be able to locate components and/or persons within the environment more quickly. The mobile device can be a type of mobile organizer, which has a dedicated application (app) for interaction with the localization system. It is also conceivable to provide a web-based application at the computer for instance, which can be accessed by the mobile device via a suitable browser.

It is preferable for the mobile device to also serve further organizational purposes, for instance as the mobile device of an input device also appropriate for registering patients. Such a mobile device/input device can be provided in addition to a console terminal of an image recording scanner, so that the input device is distanced from the console terminal. The input device can be designed to enter patient data. In practice this can be an input device as described by DE 10 2014 209 649 A1, for instance.

It is also expedient for the mobile device itself to be a localizable additional object that is provided with a transmit device. The mobile device can then also be localized within the scope of the inventive method, which enables access to navigation applications for instance, as is explained in more detail below.

In an embodiment of the invention position information relating to certain components or persons is selected on the basis of a search criterion predetermined at the user side, and provided as an output in the form of a list. While it is basically possible to list all components and/or persons who have an integrated transmit device and/or transmit device arranged thereupon with their current location via a suitable user interface, it is preferable to provide a search function, which permits certain sought components and/or persons to be located in a targeted manner. For instance, a search criterion can relate to a description, with which a component and/or a person (and/or possibly an additional object) is assigned by registration to a certain item of identification information. A description of this type can be an information subset that structures the description, for instance a category of components (local coil, patient couch, . . . ) and the like. This permits clear user interfaces that are appropriately adjusted for realization of the search function, in order to define the search criterion.

It is preferable for position information to be emitted at least partially in a map of the environment, particularly on the mobile device, preferably together with a separate position indicator on a mobile device itself provided with a transmit device. In a user interface a map of the environment, for instance a schematic layout drawing of the radiology department, can be used to improve the orientation of users. If a mobile device such as a tablet is used, which is itself equipped with a transmit device, is it possible to identify on the map where the mobile device actually is and the sought component/person in relation thereto. This permits an improved estimation also of one's own location.

In this context the user can be navigated through the environment to a transmit device assigned to a selected component and/or a selected person. Whenever an option exists for the user of localizing himself or herself within the environment, by a mobile device provided with a transmit device or a transmit device assigned to the user himself or herself, it is thus possible also to realize a navigation functionality, which emits movement instructions and/or represents an optimal path to the sought component/sought person. A particularly efficient navigation is enabled in this way when components/persons are located.

In addition to the method, the present invention also encompasses a localization system for localizing optional and/or exchangeable components of at least one image recording scanner and/or of persons assigned to the image recording scanner in a spatial environment around the location of the image recording scanner. The system includes transmit devices arranged or which can be arranged on the components and/or persons and receive devices (preferably stationary) in the environment, and a computer designed to determine an item of position information for each transmit based on at least one localization signal received by at least one receive device, that identifies the transmit device. All embodiments relating to the inventive method apply analogously to the inventive localization system, with which the advantages already cited can consequently also be obtained.

DESCRIPTION OF THE PREFERRED EMBODIMENTS

Figure 1:
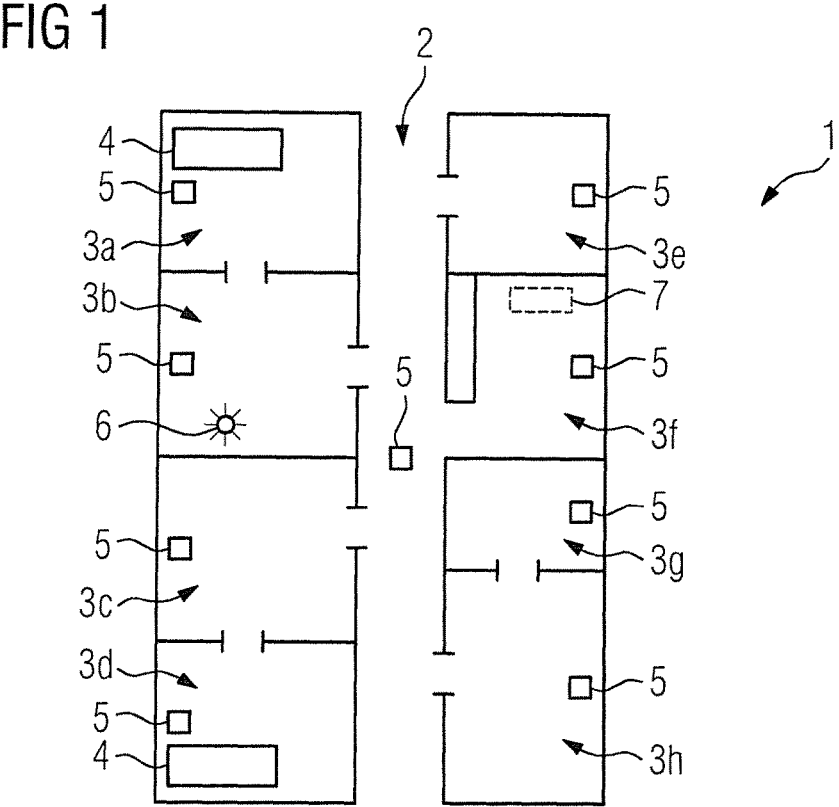
FIG. 1 shows an environment in which the inventive method can be used.

FIG. 1 is a block diagram of an environment 1, here a radiology department, in which the inventive method can be performed. A number of rooms 3a to 3h are available starting from a corridor 2 which likewise forms a room. Here rooms 3a and 3e are examination rooms, in which an image recording scanner 4 is thus disposed. The image recording scanner can be a magnetic resonance apparatus for instance, or an x-ray apparatus, for instance a CT device. Waiting rooms, rooms 3b and 3c, are assigned to each of the examination rooms 3a, 3d. Room 3e is a common room for personnel, a reception where patients can register is accommodated in room 3f. Rooms 3h, 3g are storage spaces for exchangeable and/or optional components of the image recording scanner 4. Each room has been provided with a receive device 5 assigned thereto, and it is also conceivable to provide a number of receive devices 5 in each of the rooms 3a to 3h and corridor 2, in order to allow, for instance, a triangulation for improved position determination also within any room 3a to 3h and/or corridor 2.

The receive devices 5 to wirelessly receive localization signals from transmit devices 6, of which, for clarity, only one is shown in FIG. 1. The transmit devices 6 are each assigned to stay with a component and/or a person, in particular a patient, and are thus usually arranged thereon, and are to be localized in the environment 1. To this end, each transmit device 6 transmits a localization signal, which also contains an item of identification information that permits the transmitting transmit device 6 to be identified, at fixed time intervals, in other words cyclically. The identification information can be a UUID for instance. The localization signals are received by the receive devices 5 at different reception strengths so that an evaluation thereof can at least determine the rooms 3a to 3h, corridor 2 in which the transmitting transmit device 6 is located. This evaluation takes place in a computing 7, indicated schematically, which can be embodied as a central server for instance. At least one database is also present at this computer 7, in which the identification information of the respective transmit devices is assigned to descriptions of the assigned component or the assigned person. This assignment results during the registration. When a new patient registers at reception, room 3f, for instance, he or she receives a transmit device 6, which is immediately registered to that patient in the computer 7. This takes place preferably within the scope of the DMWL. When the examination of the patient is concluded and that patient leaves the radiology department, he or she hands the transmit device 6 back again and is correspondingly deregistered. A corresponding registration or deregistration is also provided for components for the image recording scanner 4. This can take place via suitable user interfaces.

The position information that can be determined from the received localization signals of the receive devices 5 by the computer 7 is stored in the computer 7 and is assigned to the corresponding component or corresponding person. In the exemplary embodiment, the position information contains a designation of at least the room 3a to 3h, corridor 2, in which the transmit device is disposed. More abstract statements are also possible, for instance whether the transmit device 6 is actually disposed in the environment 1 or in a sub-environment of the environment 1. If a sufficient number of receive devices 5 are provided, the position information can also specify a more precise position within rooms 3a to 3h, corridor 2, for instance by triangulation on the basis of the reception strengths.

Since all components are also registered in the computer 7, the computer 7 monitors whether the components are constantly staying in sub-environments of the environment 1 assigned thereto or whether they can actually be found within the environment 1. If a component leaves the sub-environment assigned thereto or even the environment 1, a warning message is emitted that indicates this state, and thus assists with preventing theft and unauthorized removal. The warning message preferably is emitted at least to the reception, room 3f.

Figure 2:
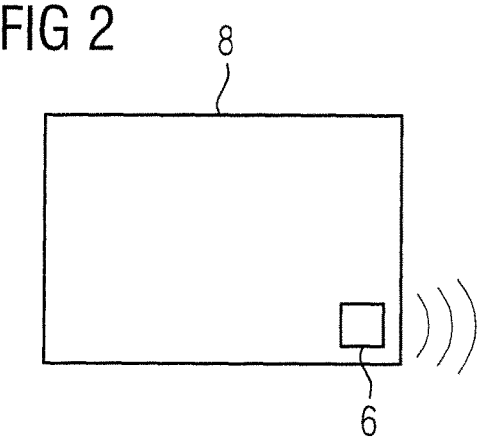
FIG. 2 is a block diagram of a component for an image recording scanner.

FIG. 2 shows, in a very simplified block diagram, a component 8, into which a transmit device 6 is integrated. The component 8 can be a local coil, for instance, a mobile detector, a patient couch, or the like.

Figure 3:
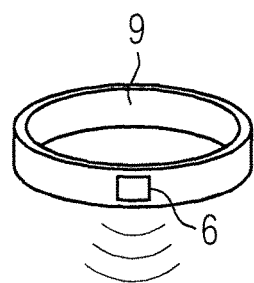
FIG. 3 is a block diagram of an armband with a transmit device.

FIG. 3 shows an example for attaching a transmit device 6 to a person. To this end, the transmit device 6 is fastened to an armband 9, which can be attached to the person, for instance a patient, at reception during registration for instance.

Since the current positions are always present in the computer 7 in the form of the position information, the positions of all components/persons, in the form of a list for instance, can be recalled and indicated on request. Specific queries can also be formulated via a search function in order to be able to locate certain components/persons in a targeted manner, for which a suitable user interface with a suitable dialog can be provided by an application, for instance on a mobile device carried by a member of staff. It is also conceivable that for the computer 7 to make a web-based application available, which can be accessed via a browser.

Figure 4:
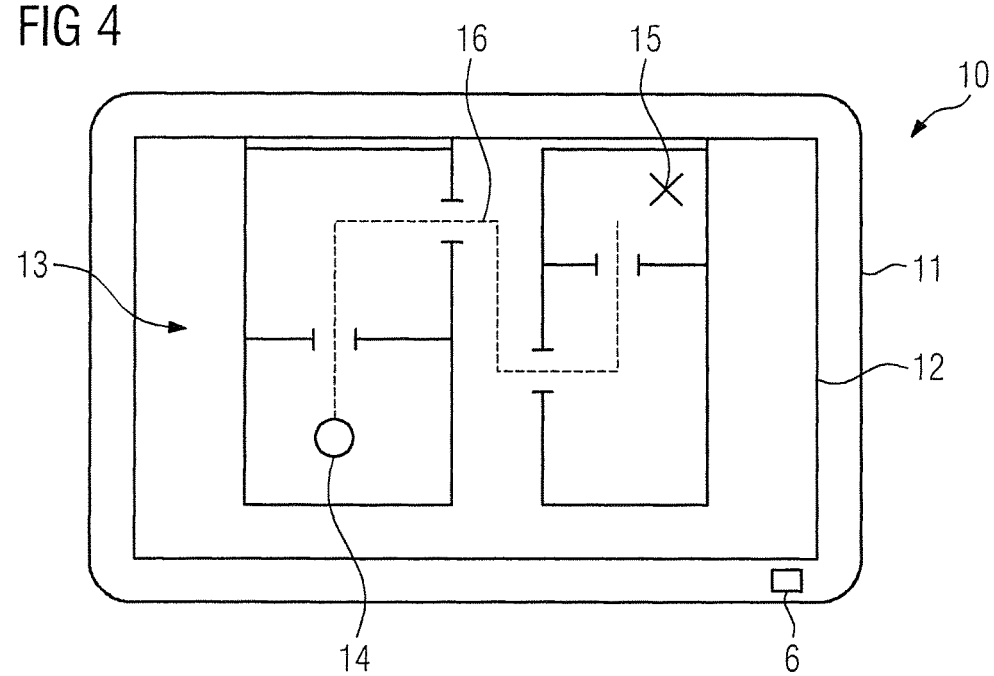
FIG. 4 shows an example of a display on a mobile device.

In the exemplary embodiment, at least some of the users of the localization system have mobile devices, here tablets, via which it is not only possible to record patient data in a function as an input device, but also component/persons can instead also be intentionally sought and corresponding position information can be output. As an example, FIG. 4 shows such a mobile device 10 in the form of a tablet 11, which as an additional object to be localized is itself provided here with a transmit device 6. The tablet 11 has a touch screen 12, on which not only user interfaces for formulating queries and thus for producing search criteria can be indicated, but also position information can be emitted which, preferably, takes place in the form of a map 13 shown schematically here, particularly with queries relating to a few objects or just one object. Because due to the transmit device 6 the mobile device 10 can itself be localized, it is possible to indicate in the map both the position 14 of the mobile device 10, thus of the user himself/herself, as well as the position 15 of a sought component/person. A local coil is currently sought as a component 8 for instance, which is disposed in the storage space 31, while the searching person is disposed in the examination space 3d in the image recording scanner 4. A navigation function is also provided, meaning that an ideal path 16 from the position 14 to the position 15 is calculated and indicated on the computer 7 or locally in the mobile device 10. In the present case the sought component 8 can be quickly located. This procedure can be transferred analogously to locating persons.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for localizing items associated with a medical image recording scanner, said method comprising:
   providing and uniquely assigning a wireless transmit device to each of a plurality of items, which are associated with operation of a medical image recording scanner, that are separable from but are situated in an environment of the medical image recording scanner, said items being selected from the group consisting of components that are optionally usable in said operation of said medical image recoding scanner, components of said medical image recording scanner that are exchangeable with other components of said medical image recording scanner, and persons to be examined by said operation of said medical image recording scanner;
   with at least one receive device situated in said environment receiving at least one localization signal from a respective transmit device that identifies the respective transmit device as a transmitting transmit device;
   providing said localization signal from said at least one receive device to a computer and, in said computer, identifying, and determining position information of, the item uniquely associated with the transmitting transmit device; and
   emitting an output signal from said computer that electronically represents said position information in a form allowing recall of the item uniquely associated with the transmitting transmit device; and
   registering said items in said computer and, if a localization signal from an item is not received, emitting a warning signal that indicates an inability to localize that item.

2. A method as claimed in claim 1 comprising mounting said at least one receive device at a fixed position, and determining said position information in said computer dependent on said fixed position of said at least one receive device.

3. A method as claimed in claim 2 comprising determining said position information in said computer dependent on a reception strength of said localization signal at said at least one receive device.

4. A method as claimed in claim 2 wherein said environment comprises a plurality of rooms, and positioning a receive device in each room and providing each receive device in said computer with an assignment of the respective room in which the respective receive device is positioned, and determining said position information in said computer dependent on the respective room to which the respective receive device is assigned that receives said localization signal.

5. A method as claimed in claim 1 comprising transmitting between said transmit devices and said at least one receive device using radio waves according to the Bluetooth standard.

6. A method as claimed in claim 1 comprising transmitting between said transmit devices and said at least one receive device using radio waves, with each transmit device transmitting a respective localization signal cyclically as a broadcast.

7. A method as claimed in claim 1 wherein said plurality of items are persons, and comprising providing each person with said wireless transmit device as an armband comprising the transmit device that is temporarily attachable to the person.

8. A method as claimed in claim 1 wherein said items are components selected from the group consisting of a patient couch, a signal detector and a local coil.

9. A method as claimed in claim 1 comprising emitting said output signal from said computer to a mobile device in communication with said computer.

10. A method as claimed in claim 9 comprising also using said mobile device as an input device to register said items in said computer.

11. A method as claimed in claim 9 comprising also providing said mobile device with one of said wireless transmit devices.

12. A method as claimed in claim 1 comprising determining said position information by executing a search in said computer based on search criterion that are predetermined.

13. A method as claimed in claim 1 comprising emitting said position information from said computer at a display in communication with said computer as a map of said environment.

14. A method as claimed in claim 13 comprising emitting said output signal from said computer to a mobile device that comprises said display, and providing said mobile device with one of said wireless transmit devices and identifying a position of said mobile device in said map at said display of said mobile device.

15. A method as claimed in claim 14 comprising providing a navigation route at said map at said mobile device that navigates a user of said mobile device through said environment to said transmitting transmit device.

16. A localization system for localizing items associated with a medical image recording scanner, comprising:

a wireless transmit device provided to, and uniquely assigned to, each of a plurality of items, which are associated with operation of a medical image recording scanner, that are separable from but are situated in an environment of the medical image recording scanner, said items being selected from the group consisting of components that are optionally usable in said operation of said medical image recoding scanner, components of said medical image recording scanner that are exchangeable with other components of said medical image recording scanner, and persons to be examined by said operation of said medical image recording scanner;

at least one receive device situated in said environment to receive at least one localization signal from a respective transmit device that identifies the respective transmit device as a transmitting transmit device;

a computer provided with said localization signal from said at least one receive device, said computer being configured to identify, and determine position information of, the item uniquely associated with the transmitting transmit device;

said computer being configured to emit an output signal that electronically represents said position information in a form allowing recall of the item uniquely associated with the transmitting transmit device; and said computer being configured to register said items in said computer and, if a localization signal from an item is not received, to emit a warning signal that indicates an inability to localize that item.

* * * * *